United States Patent [19]

Hamashima et al.

[11] 4,254,119

[45] Mar. 3, 1981

[54] 3-UNSUBSTITUTED-3-CEPHEM COMPOUNDS

[75] Inventors: Yoshio Hamashima, Kyoto; Wataru Nagata, Nishinomiya, both of Japan

[73] Assignee: Shionogi & Co., Ltd., Osaka, Japan

[21] Appl. No.: 74,811

[22] Filed: Sep. 11, 1979

[30] Foreign Application Priority Data

Sep. 20, 1978 [JP] Japan .................. 53/115498

[51] Int. Cl.³ .................. A61K 31/545; C07D 501/20
[52] U.S. Cl. ........................ 424/246; 544/22
[58] Field of Search ................ 544/22; 424/246

[56] References Cited

U.S. PATENT DOCUMENTS 4,152,433  5/1979  Kamiya et al. .................. 544/22

*Primary Examiner*—Paul M. Coughlan, Jr.
*Attorney, Agent, or Firm*—Wenderoth, Lind & Ponack

[57] ABSTRACT

Antibacterial compounds represented by the following formula including their pharmaceutically acceptable salts and esters; process for preparing them; pharmaceutical preparation comprising them; and method for combating infections by administering them:

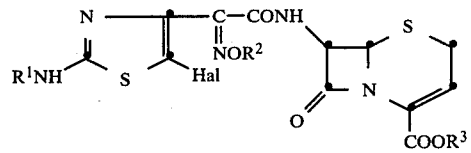

(wherein
Hal is halogen;
$R^1$ is hydrogen or an amino-protecting group;
$R^2$ is alkyl; and
$R^3$ is hydrogen or a carboxy-protecting group.)

44 Claims, No Drawings

3-UNSUBSTITUTED-3-CEPHEM COMPOUNDS

SUMMARY OF THE INVENTION

This invention relates to 7-[2-(2-amino-5-halo-4-thiazolyl)-2-alkoxyiminoacetamido]-3-cephem-4-carboxylic acids and their amino-protected or carboxy-protected derivatives directed to convenience of synthesis or to modification of pharmacological character e.g. improvement of enteral absorption, alteration of distribution in body, prolongation of activity, and so forth.

Compounds of this invention are shown by the following chemical formula:

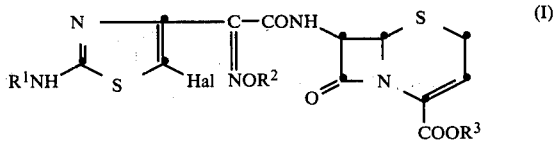

(wherein
Hal is halogen;
$R^1$ is hydrogen or an amino-protecting group;
$R^2$ is alkyl; and
$R^3$ is hydrogen or a carboxy-protecting group.)

BACKGROUND OF THE INVENTION

7β-[α-(2-amino-5-halo-4-thiazolyl)-α-alkoxyiminoacetamido]-cephalosporins have been disclosed in Japanese published patent application No. 52195/1976 (TAKEDA) excluding 3-unsubstituted cephem compounds. A description was also made in Japanese published patent application No. 149,296/1976 (TAKEDA) on cephem and penam compounds having an α-(2-amino-5-halo-4-thiazolyl)-α-alkoxyiminoacetamido group as a side chain, but no specific disclosure has been found on a 3-unsubstituted-3-cephem-4-carboxylic acid nucleus. Further, this paper mentioned no bactericidal activity of the compounds. Japanese published patent application No. 13,0691/1978 (HOECHST) discloses α-(2-amino-5-unsubstituted-4-thiazolyl)-α-alkoxyiminoacetamido-3-unsubstituted-3-cephem compounds in their scope but failed to support 3-unsubstituted-3-cephem nucleus with scientific data, in spite of detailed disclosure on other types of cephem nuclei.

Now, high antibacterial activity has been found on Compounds (I) having high antipseudomonal activity over non-halogenaged thiazolyl derivatives and 3-alkyl, 3-halo, 3-acyloxymethyl, and 3-heterothiomethyl derivatives as is disclosed later. Thus, the present inventors declare their invention.

After priority date of this application, Japanese published patent application No. 52,096/1979 (FUJISAWA) was published covering Compounds (I) carrying no halogen at the 5-position off thiazole ring. This compound has been used as standard in our priority application.

DETAILED EXPLANATION OF THE INVENTION

In the aforementioned definition, halogen shown by Hal can be fluorine, chlorine, bromine, etc.

The amino-protecting group shown by $R^1$ can be acyl such as alkanoyl optionally substituted by halogen (e.g. formyl, acetyl, chloroacetyl, trifluoroacetyl), alkoxycarbonyl optionally substituted by halogen or alkanesulfonyloxycarbonyl (e.g. t-butoxycarbonyl, chclopropylmethoxycarbonyl, methanesulfonyloxyethoxycarbonyl), aralkoxycarbonyl (e.g. benzyloxycarbonyl, nitrobenzyloxycarbonyl), alkylsilyl (e.g. trimethylsilyl, methoxydimethylsilyl), alkylstannyl, oxoalkylene (e.g. alkoxycarbonyloxopropenyl, carbamoyloxopropenyl, acetylpropenyl, oxotetrahydrofuranylidenethyl, oxocyclopentenyl), aralkylidene (e.g. ethylidene), aralkylidene (e.g. benzal), or other conventional amino-protecting groups. When $R^1$ is hydrogen, Compounds (I) can form acid-addition salts (with e.g. hydrochloric acid, nitric acid, sulfuric acid, alkanesulfonic acid, arylsulfonic acid, acetic acid, citric acid, thiocyanic acid, trifluoroacetic acid). These salts are also included in the scope of this invention.

The alkyl shown by $R^2$ can be $C_1$ to $C_6$ alkyl (e.g. methyl, ethyl, propyl, i-butyl).

The carboxy-protecting group shown by $R^3$ can be one of various protecting groups conventional in the field of penicillin and cephalosporin chemistry, including alkyl optionally substituted by halogen, alkoxy, alkanoyloxy, alkoxycarbonyl, or alkanesulfonyl (e.g. methyl, ethyl, t-butyl, cyclopropylmethyl, cyclopropylethyl, trichloroethyl, methoxymethyl, acetoxymethyl, butyryloxyethyl, ethoxycarbonyloxyethyl, methanesulfonylethyl, diacetylmethyl), aralkyl (e.g. benzyl optionally substituted by halogen, alkoxy, nitro, hydroxy, alkyl, diphenylmethyl, alkoxydiphenylmethyl, trityl, anthranylmethyl, phenacyl, halophenacyl, phthalidyl), aryl (e.g. phenyl, indanyl, naphthyl, pentachlorphenyl, pyridyl), alkylsilyl (e.g. trimethylsilyl, ethylenedioxymethylsilyl), alkylstannyl (e.g. trimethylstannyl), and other esters and alkali metal (e.g. lithium, sodium, potassium), light metal (e.g. magnesium, calcium, aluminum), organic base (e.g. triethylamine, morpholine, N-methylmorpholine, dicyclohexylamine, pyridine, quinoline, dimethylaniline) salts and the like. Other equivalent carboxy-protecting groups e.g. amides, anhydrides, etc. are included in the scope of this invention as well as said esters and salts.

Especially important are compounds having fluorine, chlorine or bromine for Hal, methyl for $R^2$, hydrogen, $C_1$ to $C_5$ alkanoyl optionally halogenated or $C_8$ to $C_{12}$ aralkoxycarbonyl for $R^1$, hydrogen, lithium, sodium, potassium, magnesium, calcium, aluminum, $C_7$ to $C_{11}$ aralkyl, or $C_2$ to $C_6$ alkanoyloxyalkyl for $R^3$.

Specific compounds are the following:
(1) $R^1=H$, $R^2=CH_3$, $R^3=H$, and $Hal=F$;
(2) $R^1=H$, $R^2=CH_3$, $R^3=H$, and $Hal=Cl$;
(3) $R^1=H$, $R^2=CH_3$, $R^3=H$, and $Hal=Br$;
(4) $R^1=H$, $R^2=CH_3$, $R^3=$phthalidyl, and $Hal=Cl$;
(5) $R^1=H$, $R^2=CH_3$, $R^3=$pivaloyloxymethyl, and $Hal=Cl$;
(6) $R^1=$carbobenzoxy, $R^2=CH_3$, $R^3=$diphenylmethyl, and $Hal=F$;
(7) $R^1=$carbobenzoxy, $R^2=CH_3$, $R^3=$diphenylmethyl, and $Hal=Cl$;
(8) $R^1=$carbobenzoxy, $R^2=CH_3$, $R^3=$diphenylmethyl, and $Hal=Br$; or
(9) $R^1=$chloroacetyl, $R^2=CH_3$, $R^3=$diphenylmethyl, and $Hal=Cl$, respectively, or when $R^3=H$, its sodium or potassium salt, or when $R^1=H$, its mineral acid salt.

SYNTHESIS (1) Amide formation

Reaction of Amine (II) or its reactive derivative with alkoxyiminoacetic acid (III) or its reactive derivative affords Compound (I).

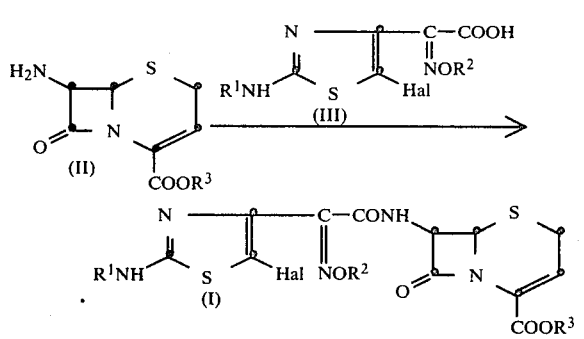

(wherein Hal, $R^1$, $R^2$, and $R^3$ are as defined above)

For this amide formation there can be applied various known amidations for cephalosporins. For example, 1 mole equivalent of amine (II) or its reactive derivative at the amino (that capable of forming an amide by reacting with an acylating reagent; e.g. trimethylsilylamine, iminohalide, iminoether, enamine, amide, isonitrile, isocyanide) can be treated with (1) acid (III) in the presence of a condensing reagent (e.g. dicyclohexylcarbodiimide, 1-ethoxycarbonyl-2-ethoxy-1,2-dihydroquinoline), or (2) a reactive derivative of acid (III) [such as acid halide (e.g. chloride, bromide), acid anhydride (e.g. mixed anhydride with alkoxyformic acid, symmetrical anhydride between two molecules of acid (III), reactive ester (e.g. dinitrophenyl ester, succinimidoyl ester), reactive amide (e.g. amide with imidazole), or other reactive derivatives of acid (III)], if required in the presence of an acid-trapping reagent (e.g. triethylamine, dimethylaniline, dimethylbenzylamine, pyridine, alkali metal hydroxide, buffer solution). The reaction can be carried out in a conventional manner preferably at $-20°$ C. to $-50°$ C. in a solvent.

(2) Oxime formation

Reaction of Glyoxylylamine (IV) with Alkoxyamine (V) affords Compound (I).

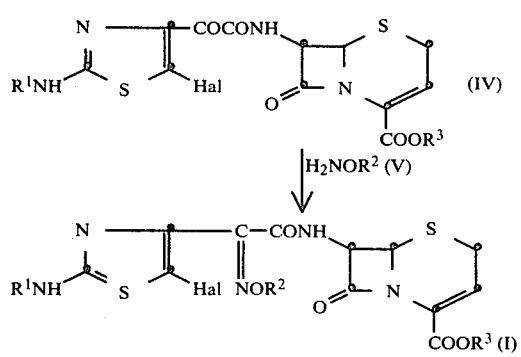

(wherein Hal, $R^1$, $R^2$, and $R^3$ are as defined above)

This oxime formation is carried out under conventional reaction conditions.

Glyoxylylamine (IV) can be prepared by reacting amine (II) with glyoxylic acid (VI) or its reactive derivative or by oxidation of glycoxylylamine (VII).

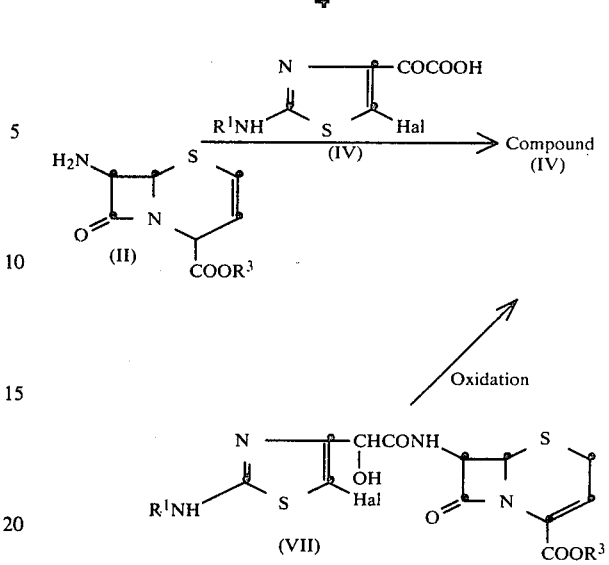

(wherein Hal, $R^1$, $R^2$, and $R^3$ are as defined above)

(3) Formation of nucleus

Replacement of the 3-substituent in conventional cephalosporins with hydrogen gives Compound (I).

For example, decarbonylation of 3-formyl-3-cephem-4-carboxylic acid derivative (VIII) or reduction of 3-(halo- or sulfonyloxy)-3-cephem-4-carboxylic acid derivative (VIII) affords Compound (I).

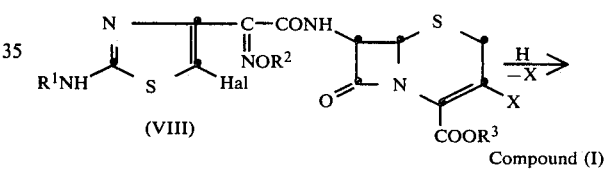

(wherein
Hal, $R^1$, $R^2$, and $R^3$ are as defined above; and
X is formyl, halogen or sulfonyloxy)

(4) Introduction of $R^2$

Reaction of the hydroxyimino compound (IX) having hydrogen as $R^2$ with an alkylating reagent (e.g. diazoalkane, dialkyl sulfate) affords Compound (I).

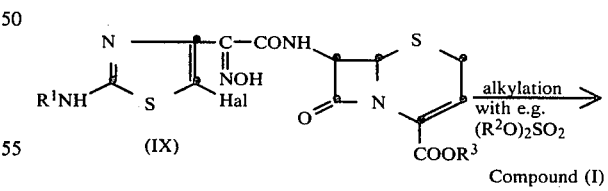

(wherein Hal, $R^1$, $R^2$, and $R^3$ are as defined above)

(5) Deprotection

Protecting group $R^1$ or $R^3$ of Compound (I) prepared as above can be deprotected by solvolysis with acid or base (when $R^1$ is salt, alkoxycarbonyl, aralkoxycarbonyl, enamine forming group, alkanoyl, etc.; or when $R^3$ is salt, alkyl ester, aralkyl ester, anhydride or silyl ester forming group, etc.), reduction (when $R^1$ is trichloroethoxycarbonyl, benzyloxycarbonyl, nitrobenzyloxycarbonyl, etc.; or when $R^3$ is trichloroethyl, nitrobenzyl, etc.), or other deprotection in penicillin or cephalosporin chemistry.

(6) Modification of the carboxy

Compounds (I) having hydrogen as $R^1$ can form an acid addition salt and those having hydrogen as $R^3$ can form a salt by reacting with a base. Salts are water soluble and suitable for use in injection.

Compounds (I) having hydrogen as $R^3$ or carboxylate salts thereof can be converted to said derivatives as esters by conventional method. Those in which $R^3$ form physiologically active esters are suitable as oral drugs.

The said reactions can be carried out under conventional conditions, generally at $-20°$ C. to $100°$ C., mainly in halogenated hydrocarbons, ethers, esters, alcohols, ketones or aqueous solvents.

EFFECTS AND USES

All Compounds (I) are novel substances showing potent antibacterial activity and useful medicines, veterinary drugs, and disinfectants. For example, they are conventionally given orally or parenterally to men or animals at a daily dose of e.g. 0.05 to 200 mg/kg body weight.

Compounds (I) are valuable antibiotics against various gram-positive bacteria (e.g. *Streptococcus pyogenes, Streptococcus pneumoniae, Bacillus subtilis, Staphylococcus aureus*) and gram-negative bacteria (e.g. *Pseudomonas aeruginosa, Escherichia coli, Klebsiella pneumoniae,* Proteus sp., Enterobacter sp., Serratia sp., Salmonella sp.), and useful as drugs for human and veterinary uses. Particularly, they are stronger against gram-negative bacteria than known compounds having similar structure but having acyloxymethyl, heterocyclylthiomethyl, or halogen at the 3-position of cephem ring. This effect is especially apparent at high inoculum size or against some cephalosporin-resistant strains of bacteria up to 200 times ratio. Further, Compounds (I) are strongest among analogous 3-norcephalorporins (e.g. corresponding 3-cephem compounds having chloro, methyltetrazolylthio, methoxy etc. at the 3-position). Compounds (I) can be used also as disinfectants for preventing decay of perishables, additives to feedstuffs, or preventing bacterial growth of hygenical materials.

Further, Compounds (I) are also useful intermediates for preparing useful antibiotics within or beyond the scope of Compounds (I).

Compounds (I), especially pharmaceutically acceptable salts, can be used in a wide variety of oral or parenteral dosage forms solely or in admixture with other coacting substances. The pharmaceutical compositions may be a mixture of 0.01 to 99% of Compound (I) with a pharmaceutical carrier which can be a solid material or liquid material in which the compounds are dissolved, dispersed, or suspended. They can be in a unit dosage form. The solid compositions can take the form of tablets, powder, dry syrups, troches, granules, capsules, pills, suppositories, or like solid preparations. The liquid compositions can take the forms of injections, ointments, dispersions, inhalant, suspensions, solutions, emulsions, syrups, or elixirs. They may be flavored, colored, and tablets, granules, and capsules may be coated.

All of diluents (e.g. starch, sucrose, lactose, calcium carbonate, kaolin); bulking agents (e.g. lactose, sugar, salt, glycine, starch, calcium carbonate, calcium phosphate, kaolin, bentonite, talc, sorbitol); binders (e.g. starch, acacia, gelatin, glucose, sodium alginate, tragacanth, carboxymethylcellulose syrup, sorbitol, polyvinylpyrrolidone); disintegrators (e.g. starch, agar, carbonates, sodium laurylsulfate); lubricant (e.g. stearic acid, talc, paraffin, boric acid, silica, sodium benzoate, polyethylene glycol, cacao oil, magnesium stearate); emulsifying agents (e.g. lecithin, sorbitan monooleate, acacia); suspending agents (e.g. sorbitol, methyl cellulose, glucose, or sugar syrup, gelatin, hydroxyethylcellulose, carboxymethylcellulose, aluminum stearate gel, hydrogenated fats); solvents (e.g. water, buffer, peanut oil, sesame oil, methyl oleate); preservatives (e.g. methyl or ethyl p-hydroxybenzoate, sorbic acid); edible coloring agents, aromatic substances, solubilizing agents, buffers, stabilizing agents, analgesics, dispersing agents, wetting agents, antioxidants, and the like can be used if the agents do not exert adverse effect on the compounds, according to the methods conventional in the art.

Compounds (I) in the form of salts, especially their alkali metal salts are readily soluble in water and conveniently used as solution for intravenous, intramuscular, or subcutaneous injection according to a conventional method. They can be dissolved in aqueous or oily solvents for injection to give a solution in an ampoule, but generally, more prolonged storage are possible by making a vial preparation containing crystals, powder, microcrystals, or lyophilizate of Compound (I) and dissolving or suspending the drug before use with the said solvents for injection. The preparation may contain preferably said preservatives. The vial preparation or injection can be given to a patient at a daily dose of e.g. 0.05 to 100 mg/kg body weight depending on the infected bacteria, condition of the patient, and interval of the administration.

Compounds (I) in the form of esters can be absorbed through the digestive organ to some extent, and can be administered to human or veterinary subjects as powder, tablets, granules, capsules, dry syrup, emulsions, solution, suspension, and like oral preparations. They may be pure compounds or a composition comprising Compounds (I) and said pharmaceutical carriers. The preparation can be made according to the methods conventional in the art, and can be administered to a patient at a daily dose of e.g. 0.5 to 200 mg/kg body weight depending on the condition of patient and the diseases.

Further, Compounds (I) can be used as suppositories, ointments for topical or ocular use, powders for topical use, and like preparations preparable according to methods well known to those skilled in the art. The preparation can contain 0.01 to 99% of Compound (I) together with a necessary amount of pharmaceutical carrier given above. A necessary amount e.g. 1 μg to 1 mg of the preparation can be applied to the affected part.

This invention also provides a method for treating or preventing human or veterinary bacterial infections by administering to the human or animal subject an effective amount of Compound (I) at a daily dose of e.g. 0.05 to 100 mg/kg body weight for injection or e.g. 0.5 to 200 mg/kg body weight for oral administration, or 1 μg to 1 mg for topical application at an interval of e.g. 3 to 12 hours.

The method is applicable for treating or preventing some diseases caused by bacteria sensitive to Compounds (I) e.g. pneumonia, bronchitis, pneumonitis, empyema, nasopharyngitis, tonsillitis, rhinitis, dermatitis, pustulosis, ulceration, fruncle, abses, wound and soft tissue infections, ear infections, osteomyelitis, septicemia, gastroenteritis, enteritis, urinary tract infections, and pyelonephritis when caused by bacteria sensitive to Compounds (I), especially by *Pseudomonas aeruginosa*.

Preferably, Compounds (I) are given to a patient in forms of pharmaceutical preparations e.g. powder, dry syrup, tablets, troches, granules, capsules, pills, suppositories, injections, ointments, dispersions, inhalant, suspensions, solutions, emulsions, syrups, and elixirs. They may be in a unit dosage form e.g. tablets, troches, capsules, injections, vials, granules, or powder in a separate container or package.

Preferable Compounds (I) for the methods and preparations are those where Hal is fluorine, chlorine, or bromine, $R^1$ is hydrogen or carbobenzoxy, $R^2$ is methyl, and $R^3$ is sodium, potassium, phthalidyl, or pivaloyloxymethyl.

Most preferable ones for the methods and preparations are following compounds:
Hal=Cl, $R^1$=H, $R^2$=CH$_3$, and $R^3$=H;
Hal=Cl, $R^1$=H, $R^2$=CH$_3$, and $R^3$=sodium;
Hal=Cl, $R^1$=H, $R^2$=CH$_3$, and $R^3$=potassium;
Hal=Cl, $R^1$=H, $R^2$=CH$_3$, and $R^3$=phthalidyl;
Hal=Cl, $R^1$=H, $R^2$=CH$_3$, and $R^3$=pivaloyloxymethyl;
Hal=F, $R^1$=H, $R^2$=CH$_3$, and $R^3$=H;
Hal=F, $R^1$=H, $R^2$=CH$_3$, and $R^3$=sodium;
Hal=F, $R^1$=H, $R^2$=CH$_3$, and $R^3$=potassium;
Hal=F, $R^1$=H, $R^2$=CH$_3$, and $R^3$=phthalidyl;
Hal=F, $R^1$=H, $R^2$=CH$_3$, and $R^3$=pivaloyloxymethyl;
Hal=Br, $R^1$=H, $R^2$=CH$_3$, and $R^3$=H;
Hal=Br, $R^1$=H, $R^2$=CH$_3$, and $R^3$=sodium;
Hal=Br, $R^1$=H, $R^2$=CH$_3$, and $R^3$=potassium;
Hal=Br, $R^1$=H, $R^2$=CH$_3$, and $R^3$=phthalidyl;
Hal=Br, $R^1$=H, $R^2$=CH$_3$, and $R^3$=pivaloyloxymethyl.

The following examples are given to show embodiments of this invention.

Table 1 shows physical constants of nine Compounds (I).

TABLE 1

Physical constants of

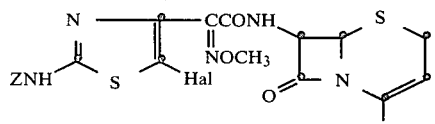

| No. | Z | Hal | $R^3$ | IR: $\nu_{max}^{CHCl_3}$ cm$^{-1}$ | NMR: $\delta_{ppm}^{CDCl_3}$ (Hz-values show coupling constants.) |
|---|---|---|---|---|---|
| 1 | H— | —F | —H | 3320,3420,1775, 1675,1632,1535, 1217,1040,(KBr) | 3.55m2H, 3.83s3H,5.07d(4.5Hz)1H, 5.80dd(4.5;9Hz)1H, 6.47m1H, 7.05brs2H, 9.55d(9Hz)1H. (CD$_3$SOCD$_3$) |
| 2 | " | —Cl | " | — | 3.57m2H, 4.02s3H, 5.07d(5Hz)1H, 5.91d(5Hz)1H, 6.62dd (4;6Hz)1H. (CDCl$_3$ CD$_3$OD) |
| 3 | " | —Br | " | 3409,3206,1775, 1675,1634,1040, (Nujol) | — |
| 4 | Cbz— | —F | —CHPh$_2$ | 3400,1780,1730, 1695,1345,1280, 1040. | 3.50m2H, 4.02s3H, 5.03d(5Hz)1H, 5.20s2H, 6.07dd(5;8 Hz)1H, 6.67m1H, 6.92s1H, 7.2–7.6m15H, 7.95d(8Hz)1H. |
| 5 | " | —Cl | " | 3400,1772,1723, 1682,1280,1038. | 3.5m2H, 4.03s3H, 5.02d(5Hz)1H, (5.12,5.24)ABq(12Hz) 2H, 6.0dd(5;8Hz)1H, 6.63m1H, 6.90s1H, 7.20–7.47m15H, 8.10d(8Hz)1H, 11.6brs1H. |
| 6 | " | —Br | " | 3406,3208,1779, 1728,1684,1548, 1284. | 3.43m2H,4.00s3H, 4.97d(4.5Hz)1H, 5.20ABq(12.5Hz)2H, 5.99dd(4.5;8.5Hz)1H, 6.65m1H, 6.92s1H, 7.05–7.80m 15H, 8.20d(8.5Hz)1H, 10.12brs1H. |
| 7 | ClAc— | —Cl | " | 1790,1775,1695, 1290,1050. | 3.53m2H, 4.05s5H, 5.03d(5Hz)1H, 6.03dd(5;9Hz)1H, 6.68m1H, 6.93s1H, 7.2–7.5m10H, 8.20d(9Hz)1H, 10brs1H. |

| No. | Z | Hal | $B^1$ | IR: $\nu_{max}^{CHCl_3}$ cm$^{-1}$ | NMR: $\delta_{ppm}^{CDCl_3}$ (Hz-values show coupling constants.) |
|---|---|---|---|---|---|
| 8 | H— | —Cl | ![phthalidyl structure] | — | 3.53m2H, 4.02s3H, 5.07d(5Hz)1H, 5.97d(5Hz)1H, 6.67m1H, 7.32s1H, 7.47–8.0m4H. (CDCl$_3$ + CD$_3$OD) |
| 9 | " | " | —CH$_2$OC=O \| t-Bu | 3400,2950,1795, 1750,1685,1615, 1460,1400,1120, 1110. | 1.18s9H, 3.00s3H, 3.08s3H, 3.53m2H, 4.03s3H, 5.02d (5Hz)1H, (5.81,5.89)ABq(6Hz)2H, 6.00d(5;9Hz)1H, 6.58m1H, 8.25s1H. |

Cbz=carbobenzoxy;
ClAc=ClCH$_2$CO—;
t-Bu=tertiary butyl.

EXAMPLE 1-1

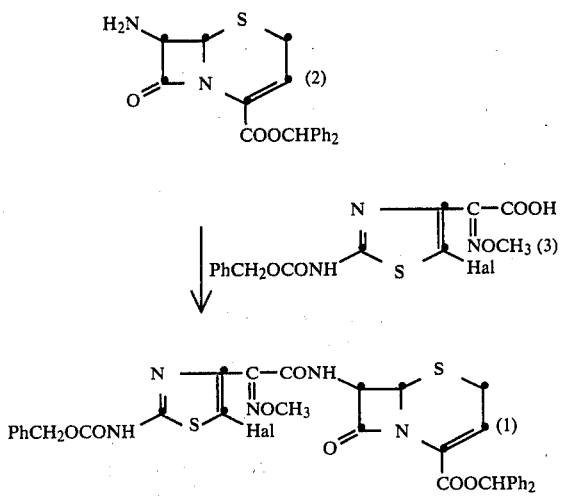

Reaction of amine (2) with acid chloride of acid (3) under conditions given in the following table gives Compound (1).

| No. | Hal | (3) (mg) | Solvent(ml) CH$_2$Cl$_2$/THF | PCl$_5$ (mg) | Time min.) | Temp. (°C.) | (2) (mg) | PyCH$_2$Cl$_2$ (μl) (ml) | | Time (min.) | Temp. (°C.) | (1) (mg) |
|---|---|---|---|---|---|---|---|---|---|---|---|---|
| 1 | Cl | 185 | 3+3 | 113 | 60 | 0 | 123 | 250 | 4 | 30 | −20 | 255 |
| 2 | Br | 272 | 0+3.5 | 165 | 45 | 0 | 200 | 146 | 4.5 | 45 | 0 | 370 |
| 3 | F | 204 | 3+0 | 134 | 50 | 0 | 145 | 200 | 4 | 30 | 5 | 271 |

(THF = tetrahydrofuran ; Py = pyridine)

Detailed procedure of the reaction No. 1 is given below as an example of similar procedures applicable to other reactions.
(No. 1)

To a suspension of 2-(2-carbobenzoxyamino-5-chloro-4-thiazolyl)-2-methoxyimimoacetic acid (185 mg) in a mixture (6 ml) of dichloromethane and tetrahydrofuran (1:1) is added phosphorus pentachloride (0.113 g) under ice-cooling, and the mixture is stirred for 60 minutes at 0° C. To the mixture is added a solution of 7-amino-3-cephem-4-carboxylic acid diphenylmethyl ester (123 mg) and pyridine (250 μl) in dichloromethane (4 ml) cooled at −20° C., and the mixture is stirred for 30 minutes at −20° C. The reaction mixture is poured into iced water, and extracted with dichloromethane. The organic layer is washed with water, diluted aqueous sodium hydrogencarbonate solution, water, and diluted aqueous phosphoric acid, dried and concentrated under reduced pressure. The residue is purified on silica gel column chromatography to give 7β-[2-(2-carbobenzoxyamino-5-chloro-4-thiazolyl)-2-methoxyiminoacetamido]-3-cephem-4-carboxylic acid dipehnylmethyl ester (255 mg).

EXAMPLE 1-2

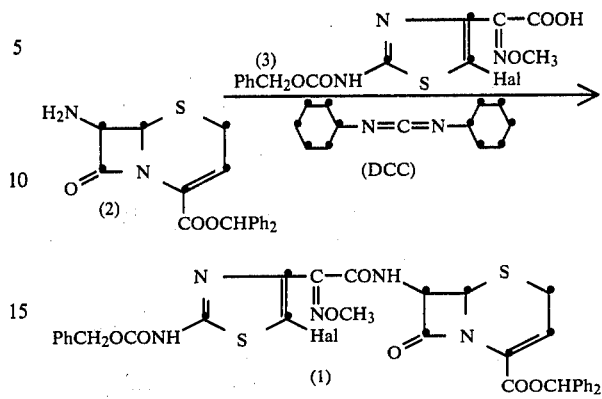

Reaction of amine (2) and acid (3) in the presence of dicyclohexylcarbodiimide (DCC) in a solvent affords objective Compound (I).

| No. | Hal | (2) (mg) | (3) (mg) | CH$_2$Cl$_2$ (ml) | DCC (mg) | Temp. (°C.) | Time (min.) | (1) (mg) |
|---|---|---|---|---|---|---|---|---|
| 1 | F | 207 | 207 | 20 | 142 | 23 | 60 | 281 |
| 2 | Cl | 103 | 103 | 10 | 75 | 25 | 60 | 163 |
| 3 | Br | 180 | 150 | 20 | 138 | 20 | 30 | 262 |

(DCC = dicyclohexylcarbodiimide)

Detailed procedure of the reaction No. 1 is given below as an example of similar procedures applicable to other reactions.
(No. 1)

To a solution of 2-(2-carbobenzoxyamino-5-fluoro-4-thiazolyl)-2-methoxyiminoacetic acid (207 mg) and 7β-amino-3-cephem-4-carboxylic acid diphenylmethyl ester (207 mg) in dichloromethane (20 ml) is added dicyclohexylcarbodiimide (142 mg), and the mixture is stirred at 23° C. for 60 minutes and concentrated to remove dichloromethane. The residue is dissolved in ethyl acetate, filtered to remove solid material, and concentrated under reduced pressure. The resultant product is purified by silica gel column chromatography to afford 7β-[2-(2-carbobenzoxyamino-5-fluoro-4-thiazolyl)-2-methoxyiminoacetamido]-3-cephem-4-carboxylic acid diphenylmethyl ester (281 mg).

EXAMPLE 1-3

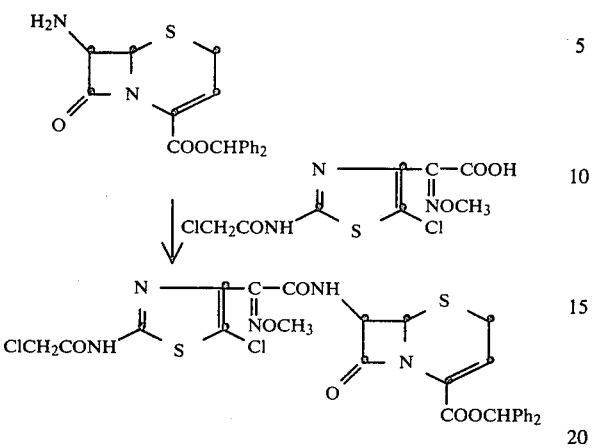

To a solution of 7β-amino-3-cephem-4-carboxylic acid diphenylmethyl ester (1.10 g) in dichloromethane (120 ml) are added a solution of 2-(2-chloroacetamido-5-chloro-4-thiazolyl)-2-methoxyiminoacetic acid (1.20 g) and N,N-dicyclohexylcarbodiimide (0.80 g), and the mixture is stirred for 30 minutes at room temperature. After concentrating to remove dichloromethane, the obtained residue is treated with a small amount of ethyl acetate and filtered to remove insoluble material. The solution is concentrated in vacuo, and the residue is purified by chromatography on silica gel affording 7β-[2-methoxyimino-2-(2-chloroacetamido-5-chloro-4-thiazolyl)acetamido]-3-cephem-4-carboxylic acid diphenylmethyl ester (1.49 g). mp. 149°–151° C. when crystallized from benzene. Similarly prepared are compounds of Table 1.

EXAMPLE 2-1

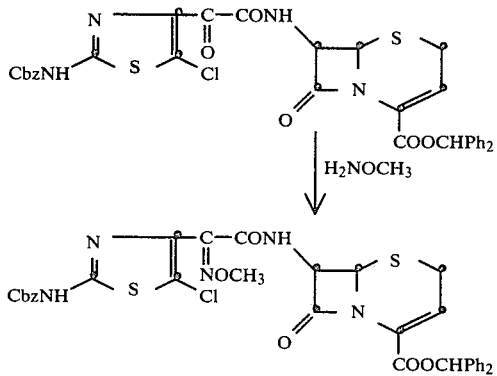

To a solution of 7β-(2-carbobenzoxyamino-5-chloro-4-thiazolyl)glyoxylylamino-3-cephem-4-carboxylic acid diphenylmethyl ester (280 mg) in ethanol (5 ml) are added triethylamine (50 μl) and methoxyamine hydrochloride (34 mg), and the mixture is stirred at room temperature for 40 minutes. Conventional work-up of the reaction mixture gives 7β-[2-(2-carbobenzoxyamino-5-chloro-4-thiazolyl)-2-methoxyiminoacetamido]-3-cephem-4-carboxylic acid diphenylmethyl ester.

EXAMPLE 2-2

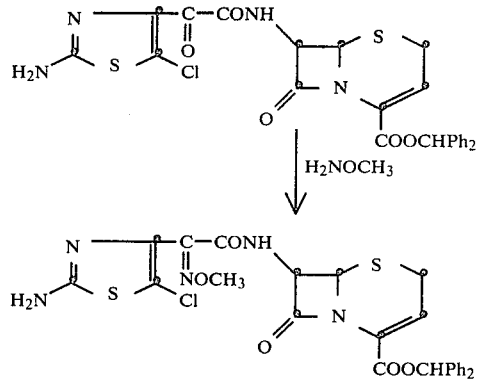

In a similar procedure to that of Example 2-1, 7β-[2-(2-amino-5-chloro-4-thiazolyl)glyoxylylamino]-3-cephem-4-carboxylic acid (276 mg) is treated with methoxyamine hydrochloride (58 mg) in methanol (5 ml) in the presence of sodium carbonate (74 mg) to afford 7β-[2-(2-amino-5-chloro-4-thiazolyl)-2-methoxyiminoacetamido]-3-cephem-4-carboxylic acid. Similarly prepared are compounds of Table 1.

EXAMPLE 3-1

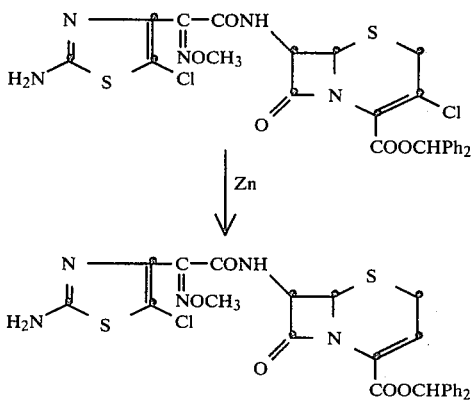

To a solution of 7β-[2-(2-amino-5-chloro-4-thiazolyl)-2-methoxyiminoacetamido]-3-chloro-3-cephem-4-carboxylic acid diphenylmethyl ester (180 mg) in dichloromethane (5 ml) are added zinc powder (120 mg) and acetic acid (1 ml), and the mixture is stirred at −10° C. for 10 minutes. The reaction mixture is filtered, poured into iced water and extracted with ethyl acetate. The extract solution is washed with aqueous sodium hydrogen carbonate solution and water, dried and concentrated. Conventional work-up of obtained residue affords 7β-[2-(2-amino-5-chloro-4-thiazolyl)-2-methoxyiminoacetamido]-3-cephem-4-carboxylic acid diphenylmethyl ester. Similarly prepared are compounds of Table 1.

EXAMPLE 4-1

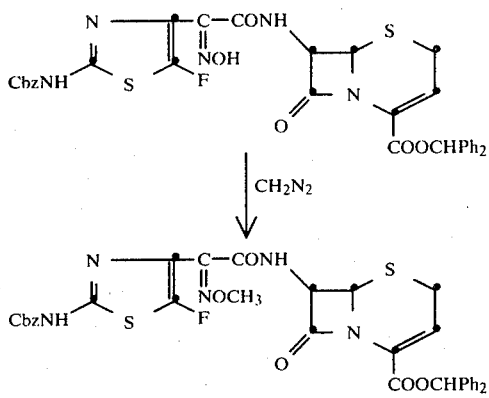

To a solution of 7β-[2-(2-carbobenzoxyamino-5-fluoro-4-thiazolyl)-2-hydroxyiminoacetamido]-3-cephem-4-carboxylic acid diphenylmethyl ester (180 mg) in dichloromethane (3 ml) is added a solution of diazomethane in ether until yellow color of the solution does no more fade out. After 30 minutes, the reaction mixture is concentrated to give 7β-[2-(2-carbobenzoxyamino-5-fluoro-4-thiazolyl)-2-methoxyiminoacetamido]-3-cephem-4-carboxylic acid diphenylmethyl ester (153 mg). Similarly prepared are compounds of Table 1.

EXAMPLE 5-1

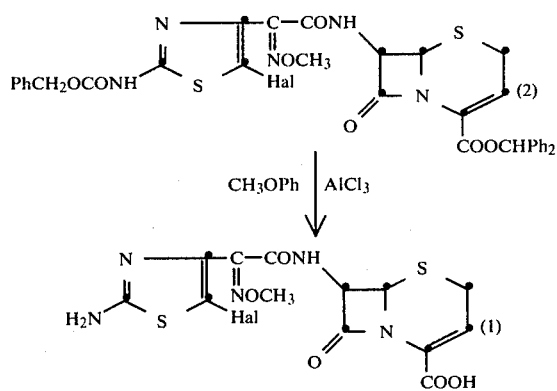

Treatment of Ester (2) with aluminium chloride and anisole in a solvent affords the objective Compound (1).

| No. | Hal | (2) (mg) | CH₃OPh (ml) | AlCl₃ (mg) | Solvent (ml) | Temp. (°C.) | Time (min.) | (1) (mg) |
|---|---|---|---|---|---|---|---|---|
| 1 | F | 270 | 4 | 510 | — | 0 | 180 | 90 |
| 2 | Cl | 216 | 5 | 400 | — | 0 | 90 | 90 |
| 3 | Br | 300 | 4 | 790 | — | 0 | 80 | 138 |

Detailed procedure of the reaction No. 2 is given below as an example of similar procedures applicable to other reactions.

(No. 2)

To a solution of 7β-[2-(2-carbobenzoxyamino-5-chloro-4-thiazolyl)-2-methoxyiminoacetamido]-3-cephem-4-carboxylic acid diphenylmethyl ester (216 mg) in anisole (5 ml) is added aluminium chloride (400 mg) under ice-cooling, and the mixture is stirred for 90 minutes at 10° C. The reaction mixture is adjusted to pH 8–9 with 5% aqueous sodium hydrogen carbonate solution, and filtered to remove separated solid. The filtrate is washed with ethyl acetate, acidified with 10% hydrochloric acid to pH 2 and extracted with methyl ethyl ketone. The extract solution is washed with saline, dried over sodium sulfate and concentrated. The obtained residue is solidified with ether, collected by filtration, and washed with ether to give 7β-[2-(2-amino-5-chloro-4-thiazolyl)-2-methoxyiminoacetamido]-3-cephem-4-carboxylic acid (93 mg). Yield: 74%.

EXAMPLE 5-2

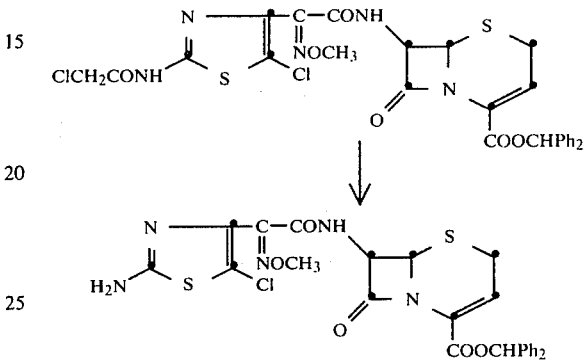

To a solution of 7β-[2-methoxyimino-2-(2-chloroacetamido-5-chloro-4-thiazolyl)acetamido]-3-cephem-4-carboxylic acid diphenylmethyl ester (330 mg) in a mixture of ethanol (5 ml) and tetrahydrofuran (5 ml) is added thiourea (152 mg), and the mixture is stirred for 4 hours. After one night, the solution is stirred with 5% aqueous sodium hydrogen carbonate solution for 10 minutes, concentrated to remove organic solvents, and extracted with ethyl acetate. The residue is subjected to silica gel chromatography to give crude 7β-[2-methoxyimino-2-(2-amino-5-chloro-4-thiazolyl)acetamido]-3-cephem-4-carboxylic acid diphenylmethyl ester (273 mg), which is stirred with anisole (0.5 ml) and trifluoroacetic acid (0.5 ml) in dichloromethane (5 ml) under ice-cooling for 1.5 hours, evaporated and treated with ethyl ether and high porous polymer to give 7β-[2-methoxyimino-2-(2-amino-5-chloro-4-thiazolyl)acetamido]-3-cephem-4-carboxylic acid (164 mg). Yield: 76.7%. This product is identical with a sample prepared by another authentic route. Similarly prepared are compounds of Table 1.

EXAMPLE 6-1

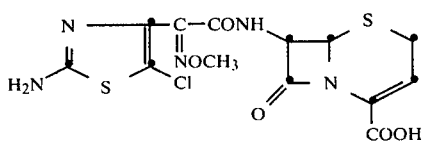

—continued

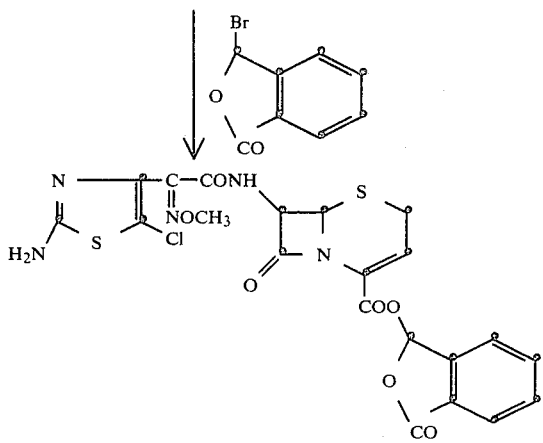

To a solution of 7β-[2-(2-amino-5-chloro-4-thiazolyl)-2-methoxyiminoacetamido]-3-cephem-4-carboxylic acid (209 mg) in N,N-dimethylformamide (5 ml) are added triethylamine (0.07 ml) and phthalidyl bromide (128 mg), and the mixture is stirred at room temperature for 20 minutes. The reaction mixture is poured into water and the separated precipitate is collected by filtration. The solid material is dissolved in ethyl acetate, washed with water, diluted aqueous sodium hydrogen carbonate solution, water, diluted aqueous phosphoric acid and water, dried, and evaporated. Purification of the residue by silica gel column chromatography gives 7β-[2-(2-amino-5-chloro-4-thiazolyl)-2-methoxyiminoacetamido]-3-cephem-4-carboxylic acid phthalidyl ester (220 mg).

—continued

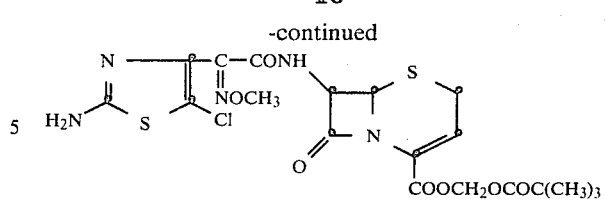

To a solution of 7β-[2-metoxyimino-2-(2-amino-5-chloro-4-thiazolyl)acetamido]-3-cephem-4-carboxylic acid potassium salt prepared from 1.16 g of the free acid and a mole equivalent of potassium 2-ethylhexanoate in N,N-dimethylformamide (7 ml) are added a small excess amount of a solution of pivaloyloxymethyl iodide in N,N-dimethylformamide (7 ml), and the mixture is stirred at room temperature for 3 hours. The reaction mixture is poured into iced water and extracted with ethyl acetate. The extract solution is purified by chromatography over silica gel (50 g) using a mixture of benzene and ethyl acetate (1:1) affording 2β-[2-methoxyimino-2-(2-amino-5chloro-4-thiazolyl)acetamido]-3-cephem-4-carboxylic acid pivaloyloxymethyl ester. Similarly prepared are compounds of Table 1.

EXAMPLE 7-1 (EXPERIMENT 1) (SODIUM SALT)

The free carboxylic acids prepared by the methods described in the preceding examples are dissolved in 0.011 N aqueous sodium hydrogen carbonate to give solutions of sodium salts and assayed minimal inhibitory concentration at 37° C. by two-fold dilution method on Agar Medium (Mühler Hinton) of pH 7 to obtain the value of the following Table 2.

TABLE 2

MIC values of 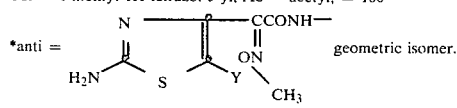

| | (inoculum size = $10^8$/ml) | | | | | | | |
|---|---|---|---|---|---|---|---|---|
| Y | F | Cl | Br | Cl* | H | H | H | H |
| Z | H | H | H | H | H | Cl | —CH$_2$STet | —CH$_2$OAc |
| Escherichia coli JC-2 | 0.1 | 1.6 | 6.3 | 100 | 0.1 | 0.4 | 0.8 | 0.2 |
| Klebsiella 363 | 0.2 | 0.8 | 3.1 | 50 | 0.2 | 1.6 | > | 3.1 |
| Proteus vulgaris No. 3 | 0.4 | 0.8 | 6.3 | > | 0.4 | > | > | > |
| Pseudomonas aeruginosa 25619 | 6.3 | 0.8 | 1.6 | 100 | 25 | > | 3.1 | 12.5 |
| Pseudomonas aeruginosa 24 | 100 | 25 | 50 | > | > | > | > | > |

Tet = 1-methyl-1H-tetrazol-5-yl; Ac = acetyl; = 100

*anti = 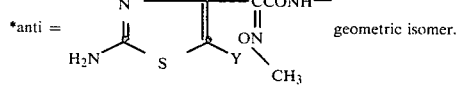 geometric isomer.

EXAMPLE 6-2

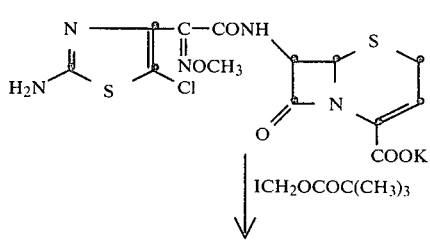

EXAMPLE 8-1

Sodium salt of 7β-[α-(2-amino-5-chloro-4-thiazolyl)-α-methoxyiminoacetamido]-3-cephem-4-carboxylic acid (1 g) in a 5 ml vial is dissolved in sterilized water for injection (1 ml) before use, and given to an adult patient suffering from mixed infection by way of intravenous injection twice a day caused by Pseudomonas aeruginosa and Escherichia coli.

EXAMPLE 8-2

Lyophilizate from a solution of 7β-[α-(2-amino-5-fluoro-4-thiazolyl)-α-methoxyiminoacetamido]-3-cephem-4-carboxylic acid (1 g) neutralized to pH 7.0 with sodium hydrogencarbonate is placed in a 150 ml vial. The lyophilizate is dissolved in sterilized water for injection (100 ml) and dripped intravenously to an adult patient immediately after or during a surgical operation for preventing and treating post operative bacterial infection.

EXAMPLE 8-3

Microcrystalline 7β-[α-(2-amino-5-bromo-4-thiazolyl)-α-methoxyiminoacetamido]-3-cephem-4-carboxylic acid (200 mg) in a 5 ml vial is suspended in sterilized water for injection containing 2 mg of procaine (2 ml), and given intramuscularly to a patient suffering from fruncle or abscess caused by *Staphylococcus aureus*.

EXAMPLE 8-4

Crystalline pivaloyloxymethyl 7β-[α-(2-amino-5-fluoro-4-thiazolyl)-α-methoxyiminoacetamido]-3-cephem-4-carboxylate (200 mg) is dissolved in sesame oil (0.25 ml) and filled in a hard gelatin capsule. Two capsules are given orally at 4 hour intervals to a patient suffering from upper respiratory tract infection caused by Klebsiella.

EXAMPLE 8-5

Powdered phthalidyl 7β-[α-(2-amino-5-chloro-4-thiazolyl)-α-methoxyiminoacetamido]-3-cephem-4-carboxylate (100 mg) is mixed well with corn starch (150 mg) and talc (10 mg), powdered, and encapsulated in a hard gelatin capsule (250 mg volume). One capsule is administered orally at 3 hour intervals to an adult patient suffering from urinary tract infection caused by *Pseudomonas aeruginosa*.

EXAMPLE 8-6

Mixed powder of 7β-[α-(2-amino-5-chloro-4-thiazolyl)-α-methoxyiminoacetamido]-3-cephem-4-carboxylic acid (10 g), lactose (50 g), corn starch (2 g), magnesium stearate (0.3 g), sucrose (10 g), and necessary amount of acacia and talc is granulated. The granule is mixed with water before use to obtain a suspension, and one teaspoonful amount of the suspension is given orally at 6 hour intervals to an infant suffering from pneumonia caused by *Klebsiella pneumoniae*.

In this specification, $R^2O$- and amidocarbonyl in the side chain are in the syn-geometric position with respect to C=N double bond unless otherwise specified. The anti-geometric isomers in this series are very weak antibacterials.

The following preparations are given to show details of preparations of some starting materials. Physical constants are given after Preparation 4.

Preparation 1

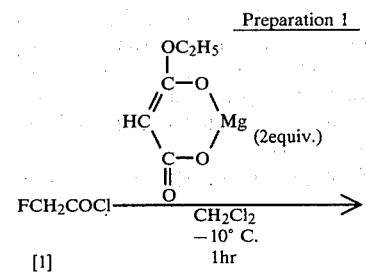

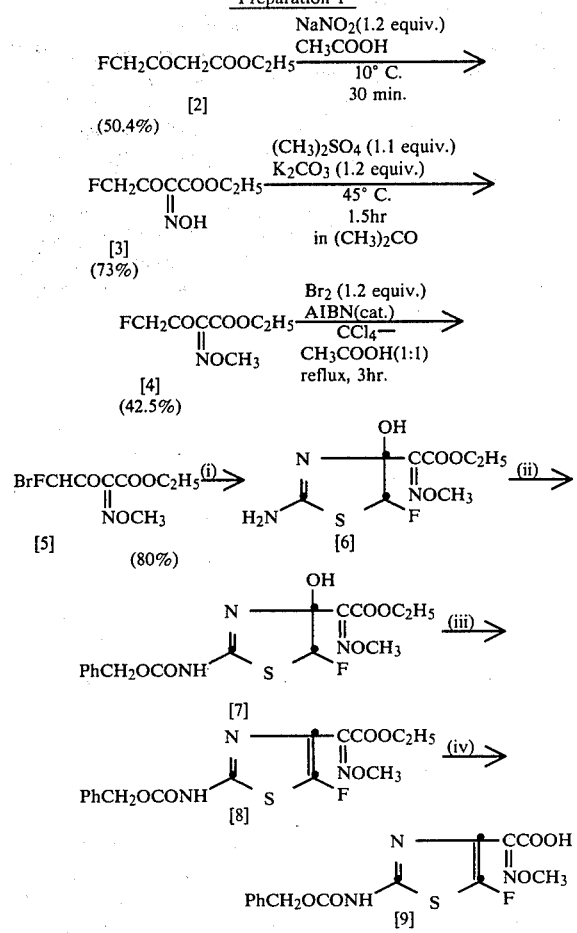

(i) To a solution of bromofluoroacetoacetic acid ester [5] (8.6 g) in ethanol (43 ml) is added thiourea (2.54 g), and the mixture is stirred at room temperature for 1.5 hours and concentrated to remove ethanol under reduced pressure. The residue is diluted with ethyl acetate, washed with diluted aqueous sodium hydrogen carbonate and water, dried and concentrated under reduced pressure. Purification of the residue (8.38 g) by silica gel column chromatography gives thiazolinecarboxylic acid ester [6] (4.26 g).

Yield: 50.5%

(ii) To a solution of thiazolinecarboxylic acid ester [6] (3.56 g) in dichloromethane (40 ml) are added benzyl chloroformate (4.6 ml) and pyridine (2.4 ml) at −10° C. The mixture is stirred for 1 hour under ice-cooling, diluted with dichloromethane, and washed successively with diluted hydrochloric acid, aqueous sodium carbonate and saline, dried over magnesium sulfate and concentrated under reduced pressure. Purification of residual oil by silica gel column chromatography gives carbobenzoxythiazoline ester [7] (4.71 g) and fluorothiazole ester [8] (1.05 g).

(iii) To a solution of carbobenzoxythiazoline ester [7] (4.71 g) in dioxane (47 ml) is added toluene-p-sulfonic acid (3.37 g), and the mixture is stirred at 60° C. for 6 hours. The reaction mixture is concentrated to remove dioxane, and obtained residue is dissolved in ethyl acetate, washed with water, dried over magnesium sulfate, concentrated, and the residue purified by silica gel column chromatography to give fluorothiazole ester [8] (2.50 g). Amounting 3.55 g Total yield: 64.7% from (ii) and (iii).

(iv) To a solution of fluorothiazole ester [8] (2.3 g) in methanol (23 ml) is added 3 N aqueous sodium hydroxide (23 ml), and the mixture is stirred at 50° C. for 30 minutes. The reaction mixture is concentrated. The obtained residue is dissolved in iced water, washed with ethyl acetate, and acidified with 10% hydrochloric acid to about pH 2. The separated precipitate is collected by filtration, washed with water, dried, washed several times with ether and triturated in a mixture of ethyl acetate and ether (1:1) to give fluorothiazolecarboxylic acid [9] (590 mg).

Yield: 28.7%

Preparation 3

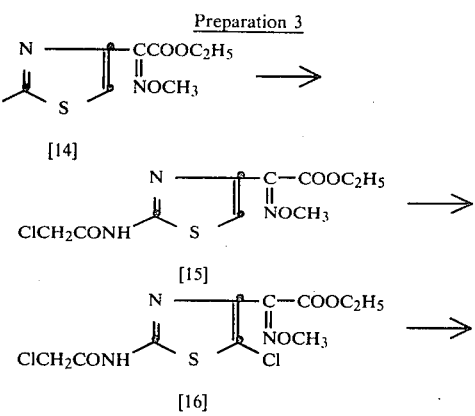

Preparation 2

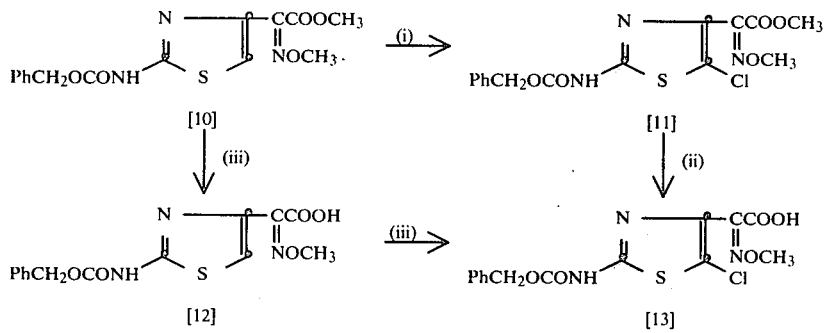

(i) To a solution of unsubstituted ester [10] (166 mg) in N,N-dimethylformamide (1 ml) is dropwise added a solution of trichloroisocyanuric acid (37 mg) in N,N-dimethylformamide (0.3 ml) at 50° C. After stirring for 30 minutes, the mixture is poured into iced water and extracted with ethyl acetate. The extract is washed with water, dried and purified by silica gel chromatography to give chloroester [11] (80 mg).

(ii) To a solution of chloroester [11] (470 mg) in acetone (5 ml) is added dropwise 1 N aqueous sodium hydroxide (5 ml) at room temperature, and the mixture is permitted to react for 40 minutes at the same temperature. The reaction mixture is neutralized with hydrochloric acid. The separated crystals are collected by filtration and recrystallized from acetone to give chlorocarboxylic acid [13] (415 mg). m.p. 186°–187° C. (decomposition).

Elemental Analysis: (for $C_{14}H_{12}N_3O_5SCl$) Calcd(%): C, 45.47; H, 3.27; N, 11.36. Found(%): C, 45.21; H, 3.20; N, 11.47.

(iii) To a solution of unsubstituted carboxylic acid [12] (3.35 g) (prepared by hydrolysis of unsubstituted ester [10] under condition analogous to above (ii)) in N,N-dimethylformamide (10 ml) is added a solution of trichloroisocyanuric acid (0.815 g) in N,N-dimethylformamide (3 ml) at 50° C., and the mixture is stirred for 30 minutes. The reaction mixture is poured into iced water. The formed precipitate is collected by filtration, dried and recrystallized from acetone to give chlorocarboxylic acid [13] (3.18 g) identical with that obtained by the procedure of above (ii). mp. 186°–187° C. (decomposition).

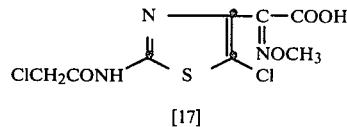

To a solution of nonhalogenated ester [14] (4.59 g) in dichloromethane (40 ml) are added pyridine (2.4 ml) and chloroacetyl chloride (2.3 ml) at −30° C., and the mixture is treated by the conventional method to obtain chloroacetylnonhalogenated ester [15] (4.77 g), m.p. 118°–119° C. when crystallized from ethyl acetate.

To a solution of chloroacetyl nonhalogenated ester [15] (4.59 g) in N,N-dimethylformamide (15 ml) warmed at 40° C. to 50° C. is added a solution of trichloroisocyanuric acid (1.29 g) in N,N-dimethylformamide (13 ml) and the mixture is stirred at the same temperature for 30 minutes. The reaction mixture is poured into iced water, and extracted with ethyl acetate. After washing with saturated saline, the extract solution is dried over magnesium sulfate and concentrated to remove the solvent and linsed with benzene to give crystals of chloroacetylchloro ester [16] (4.05 g), mp. 125°–126° C.

To a solution of potassium hydroxide (3.0 g) in a mixture of water (10 ml) and ethanol (100 ml) is added chloroacetylchloro ester [16] (3.3 g), and the mixture is stirred for about 1 hour at room temperature until transparent. After evaporation of ethanol in vacuo, the residual solution is mixed with a small amount of water, washed with ethyl acetate, and acidified with 10% hydrochloric acid down to pH 2.0 to separate crystals (1.59 g) of chloroacetylchloro acid [17], m.p. 159°–160° C.

Preparation 4

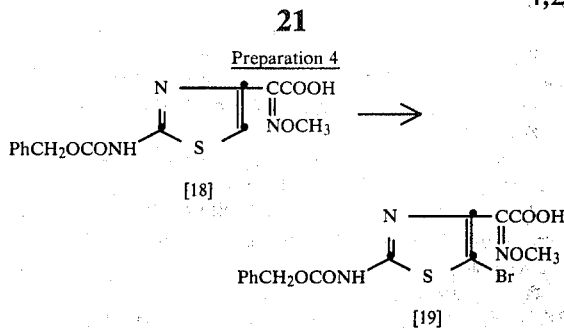

To a suspension of unsubstituted carboxylic acid [18] (506 mg) in dichloromethane (8 ml) is dropwise added 3% solution of bromine in acetic acid (7.85 ml) under ice-cooling over 45 minutes period. After stirring at 0° C. for 1 hour, the mixture is filtered to collect the precipitate, which is washed with benzene to give bromocarboxylic acid [19] (190 mg). Mother liquor gives further 258 mg amount of the same product. Totally 448 mg. Yield: 72%. About 101 mg amount of anti-isomer is produced as a byproduct.

NMR: $\delta_{ppm}^{CD3SOCD3}$ 3.82s3H, 5.07s2H, 7.20s5H.

IR: $\nu_{max}^{Nujol}$ 3253, 1742, 1705, 1245, 1049, 739 cm$^{-1}$.

TABLE 3
Physical constants of intermediates

| Compound No. | IR: $\nu_{max}^{CHCl_3}$ cm$^{-1}$ | NMR: $\delta_{ppm}^{CDCl_3}$ (Hz-values show coupling constants) |
|---|---|---|
| [8] | — | 1.33t(7Hz)3H, 3.95s3H, 4.37q (7Hz)2H, 5.22s2H, 7.33s5H, 8.78 brs1H. |
| [9] | — | 3.93s3H, 5.25s2H, 7.37s5H (CH$_3$COCD$_3$—CD$_3$OD(8:1). |
| [11] | 3395, 1737, 1546, 1258, 1037. | 3.87s3H, 3.95s3H, 5.20s2H, 7.33s5H. |
| [13] | — | 3.93s3H, 5.23s2H, 7.37s5H, 12.37s1H (CD$_3$SOCD$_3$). |
| [16] | 3350, 1730, 1685, 1535. | 1.38t(7Hz)3H, 4.03s3H, 4.23s2H, 4.40q(7Hz)2H. |
| [17] | — | 4.40s3H, 4.27s2H (CD$_3$OD) |
| [19] | 3173, 1723, 1718, 1312, 1279, 1046, 721 (Nujol). | 3.77s3H, 5.08s2H, 7.26s5H (CD$_3$SOCD$_3$). |

What we claim is:

1. A compound of the formula

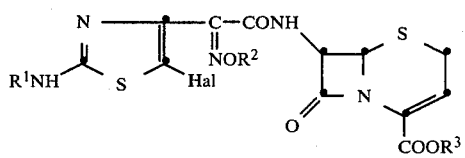

wherein Hal is halogen;
R$^1$ is hydrogen, C$_1$ to C$_5$ alkanoyl which is optionally halogenated, or C$_8$ to C$_{12}$ aralkoxycarbonyl;
R$^2$ is C$_1$ to C$_6$ alkyl; and
R$^3$ is hydrogen, alkali metal, magnesium, calcium, aluminum, C$_7$ to C$_{11}$ aralkyl, or C$_2$ to C$_6$ alkanoyloxyalkyl
or, when R$^1$ is hydrogen, a pharmaceutically acceptable acid addition salt thereof.

2. A compound claimed in claim 1, wherein Hal is fluorine, chlorine, or bromine.

3. A compound claimed in claim 1, wherein R$^1$ is hydrogen or a mineral acid addition salt thereof.

4. A compound claimed in claim 1, wherein R$^1$ is C$_1$ to C$_5$ alkanoyl which is optionally halogenated or C$_8$ to C$_{12}$ aralkoxycarbonyl.

5. A compound claimed in claim 1, wherein R$^2$ is methyl.

6. A compound claimed in claim 1, wherein R$^3$ is hydrogen, lithium, sodium, potassium, magnesium, calcium, or aluminum.

7. A compound claimed in claim 1, wherein R$^3$ is C$_7$ to C$_{11}$ aralkyl or C$_2$ to C$_6$ alkanoyloxyalkyl.

8. A compound claimed in claim 1, wherein Hal=F, R$^1$=H, R$^2$=CH$_3$, and R$^3$=H.

9. A compound claimed in claim 1, wherein Hal=F, R$^1$=H, R$^2$=CH$_3$, and R$^3$=sodium.

10. A compound claimed in claim 1, wherein Hal=F, R$^1$=H, R$^2$=CH$_3$, and R$^3$=potassium.

11. A compound claimed in claim 1, wherein Hal=Cl, R$^1$=H, R$^2$=CH$_3$, and R$^3$=H.

12. A compound claimed in claim 1, wherein Hal=Cl, R$^1$=H, R$^2$=CH$_3$, and R$^3$=sodium.

13. A compound claimed in claim 1, wherein Hal=Cl, R$^1$=H, R$^2$=CH$_3$, and R$^3$=potassium.

14. A compound claimed in claim 1, wherein Hal=Br, R$^1$=H, R$^2$=CH$_3$, and R$^3$=H.

15. A compound claimed in claim 1, wherein Hal=Br, R$^1$=H, R$^2$=CH$_3$, and R$^3$=sodium.

16. A compound claimed in claim 1, wherein Hal=Br, R$^1$=H, R$^2$=CH$_3$, and R$^3$=potassium.

17. A compound claimed in claim 1, wherein Hal=Cl, R$^1$=H, R$^2$=CH$_3$, and R$^3$=phthalidyl.

18. A compound claimed in claim 1, wherein Hal=Cl, R$^1$=H, R$^2$=CH$_3$, and R$^3$=pivaloyloxymethyl.

19. A compound claimed in claim 1, wherein Hal=F, R$^1$=carbobenzoxy, R$^2$=CH$_3$, and R$^3$=diphenylmethyl.

20. A compound claimed in claim 1, wherein Hal=Cl, R$^1$=carbobenzoxy, R$^2$=CH$_3$, and R$^3$=diphenylmethyl.

21. A compound claimed in claim 1, wherein Hal=Br, R$^1$=carbobenzoxy, R$^2$=CH$_3$, and R$^3$=diphenylmethyl.

22. An antibacterial composition comprising a bactericidally effective amount of a compound according to claim 1 and a pharmaceutically acceptable carrier.

23. A composition according to claim 22 containing 0.01% to 99% of the active compound.

24. A composition according to claim 23 in dosage unit form.

25. A composition according to claim 24 suitable for injection.

26. A composition according to claim 25 in a form suitable for injection in an ampule or vial.

27. A composition according to claim 25 in the form of powder, crystals, microcrystals or lyophilizate in a vial.

28. A composition according to claim 25, wherein Hal=F, R$^1$=H, R$^2$=CH$_3$, and R$^3$=sodium or potassium.

29. A composition according to claim 25, wherein Hal=Cl, R$^1$=H, R$^2$=CH$_3$, and R$^3$=sodium or potassium.

30. A composition according to claim 25, wherein Hal=Br, R$^1$=H, R$^2$=CH$_3$, and R$^3$=sodium or potassium.

31. A composition according to claim 24 suitable for enteral administration.

32. A composition according to claim 31 in the form of capsule, tablet or dry syrup.

33. A composition according to claim 31, wherein Hal=Cl, $R^1$=H, $R^2$=CH$_3$, and $R^3$=phthalidyl.

34. A composition according to claim 31, wherein Hal=Cl, $R^1$=H, $R^2$=CH$_3$, and $R^3$=pivaloyloxymethyl.

35. A method for treating human or veterinary bacterial infection or for preventing post operative infection comprising the administration to a patient of a bactericidally effective amount of a compound according to claim 1.

36. A method according to claim 35 wherein the bacterial infection is pneumonia, bronchitis, pneumonitis, empyema, nasopharyngitis, tonsillitis, rhinitis, dermatitis, pustulosis, ulceration, absess, wound and soft tissue infection, ear infections, osteomyelitis, septicemia, gastroenteritis, enteritis, urinary tract infections, fruncle, or pyelonephritis, when caused by bacteria sensitive to the active compound.

37. A method according to claim 35, wherein the compound is administered by injection at a daily dose of 0.05 to 100 mg per kilogram body weight.

38. A method according to claim 35, wherein the compound is administered orally at a daily dose of 0.5 to 200 mg per kilogram of body weight.

39. A method according to claim 35, wherein the compound is administered topically at a daily dose of 1 μg to 1 mg.

40. A method according to claim 35, wherein Hal=F, $R^1$=H, $R^2$=CH$_3$, and $R^3$=sodium or potassium.

41. A method according to claim 35, wherein Hal=Cl, $R^1$=H, $R^2$=CH$_3$, and $R^3$=sodium or potassium.

42. A method according to claim 35, wherein Hal=Br, $R^1$=H, $R^2$=CH$_3$, and $R^3$=sodium or potassium.

43. A method according to claim 35, wherein Hal=Cl, $R^1$=H, $R^2$=CH$_3$, and $R^3$=phthalidyl.

44. A method according to claim 35, wherein Hal=Cl, $R^1$=H, $R^2$=CH$_3$, and $R^3$=pivaloyloxymethyl.

* * * * *

Notice of Adverse Decision in Interference

In Interference No. 101,294, involving Patent No. 4,254,119, Y. Hamashima and W. Nagata, 3-UNSUBSTITUTED-3-CEPHEM COMPOUNDS, final judgement adverse to the patentees was rendered Mar. 27, 1985, as to claims 1-7, 14, 22 and 24.

[*Official Gazette September 17, 1985.*]